US008460376B2

(12) United States Patent
Donitzky et al.

(10) Patent No.: US 8,460,376 B2
(45) Date of Patent: Jun. 11, 2013

(54) INTRAOCULAR LENS

(75) Inventors: Christof Donitzky, Eckental (DE); Klaus Vogler, Eckental (DE)

(73) Assignee: Wavelight Laser Technologie AG, Erlangen (DE)

( * ) Notice: Subject to any disclaimer, the term of this patent is extended or adjusted under 35 U.S.C. 154(b) by 0 days.

(21) Appl. No.: 11/915,001

(22) PCT Filed: May 17, 2006

(86) PCT No.: PCT/EP2006/004668
§ 371 (c)(1),
(2), (4) Date: Jun. 12, 2008

(87) PCT Pub. No.: WO2006/125556
PCT Pub. Date: Nov. 30, 2006

(65) Prior Publication Data
US 2008/0306589 A1    Dec. 11, 2008

(30) Foreign Application Priority Data

May 27, 2005    (EP) ...................................... 05011483

(51) Int. Cl.
*A61F 2/16*    (2006.01)
(52) U.S. Cl.
USPC .......................... 623/6.22; 623/6.24; 623/6.37
(58) Field of Classification Search
USPC ............................................. 623/6.11–6.62
See application file for complete search history.

(56) References Cited

U.S. PATENT DOCUMENTS

| | | | |
|---|---|---|---|
| 4,373,218 A | 2/1983 | Schachar | |
| 4,787,903 A | 11/1988 | Grendahl | |
| 5,171,266 A | 12/1992 | Wiley et al. | |
| 5,443,506 A | 8/1995 | Garabet | |
| 6,369,954 B1 | 4/2002 | Berge et al. | |
| 6,638,304 B2 * | 10/2003 | Azar | 623/6.22 |
| 6,730,123 B1 | 5/2004 | Klopotek | |
| 2003/0060878 A1 | 3/2003 | Shadduck | |
| 2004/0169932 A1 | 9/2004 | Esch et al. | |
| 2006/0155372 A1 * | 7/2006 | Coroneo | 623/4.1 |

FOREIGN PATENT DOCUMENTS

| | | |
|---|---|---|
| CA | 2306249 A1 | 4/1999 |
| EP | 1019758 B1 | 3/2002 |
| WO | WO 2005088388 A1 * | 9/2005 |

OTHER PUBLICATIONS

International Patent Cooperation Treaty Patent Application PCT/EP2006/004668 International Search Report and Written Opinion of the International Searching Authority of Oct. 19, 2006.
Stieglitz et al., "Microsystem Integration Techniques for Intraocular Vision Prostheses Using Flexible Polyimide Foils", Proceedings of MICRO.tec. 2000, pp. 467-472.
Laube et al., "Optical Energy Transfer for Intraocular Microsystems Studied in Rabbits", Graefe's Arch Clin Exp Ophthalmol (2004) 242: pp. 661-667.
Berge et al., "Variable Focal Lens Controlled by an External Voltage: An Application of Electrowetting", Eur. Phys. J. E. 3, (2000) pp. 159-163.

(Continued)

*Primary Examiner* — David H Willse
*Assistant Examiner* — Javier Blanco
(74) *Attorney, Agent, or Firm* — Haynes and Boone, LLP

(57) ABSTRACT

An intraocular lens (10) is configured so that it can be incorporated into the capsule of an eye and its refractive power can be modified by the application of electrical voltages.

13 Claims, 1 Drawing Sheet

OTHER PUBLICATIONS

Krupenkin et al., "Tunable Liquid Microlens", Applied Physics Letters, vol. 82, No. 3, Jan. 20, 2005, pp. 316-318.
Kuiper et al., "Variable-Focus Liquid Lens for Miniature Cameras", Applied Physics Letters, vol. 85, No. 7, Aug. 16, 2004, pp. 1128-1130.
Hecht, Optics—Second Edition, Chapter 5: Geometrical Optics-Paraxial Theory, Addison-Wesley Publishing Company, 1985, p. 138.
Sachs et al., "Retinal Replacement—the Development of Microelectronic Retinal Prostheses—Experience with Subretinal Implants and New Aspects", Graefe's Arch Clin Exp Ophthalmol (2004) 242: pp. 717-723.
"Eine Prothese zum Sehen", Augenlicht Jan. 2003.
Messner, "Intraokularlinsen", Der Augenspiegel, Jul.-Aug. 2002, pp. 28-34.
Dick, "Neue Multifokallinsen, Individuelle Losungen and Postoperative Funktionalitat", Der Augenspiegel, Sep. 2004, pp. 42-47.
Walter, "Die Implantation von Sehprothesen bei Progressiven Netzhautdystrophien", Der Augenspiegel, Nov. 2004, pp. 32-35.
European Patent Application No. 05011483.4 Search Report of Mar. 1, 2006.
Japanese Patent Office, Office Action dated Nov. 22, 2011, Application No. 2008-512736, 5 pages including English Translation.

* cited by examiner

INTRAOCULAR LENS

CROSS-REFERENCE

This application was originally filed as Patent Cooperation Treaty Application Number PCT/EP2006/004668 filed May 17, 2006, which claims priority of European Application Number 05011483.4, filed May 27, 2005.

The invention relates to an intraocular lens, which is suitable for being fitted into a human eye.

BACKGROUND

Intraocular lenses are widely known in opthalmology; for example, intraocular lenses are implanted in the event of opacification of the originally clear eye lens (cataract).

Age-related long-sightedness (presbyopia) is a particular problem in opthalmological, cf. for example the article "Intraokularlinsen", in DER AUGENSPIEGEL, July-August 2002: 28-34. The age-related loss of elasticity of the natural eye lens prevents adaptation of its refractive power and therefore accommodation of the eye to objects lying at close range in front of the eye, and sharp imaging thereof or the retina. Although the loss of accommodation ability can be corrected by reading glasses, this however entails the known outlay and inconveniences.

The prior art reveals a variety of attempts to resolve the problem of presbyopia:

For instance, there has been an attempt to displace artificial intraocular lenses (IOLs) by the action of the ciliary muscle of the eye (cf. the article cited above in "Der Augenspiegel"). This has, however, achieved only insufficient displacement of the IOL in the axial direction (conventionally referred to as the z axis) and therefore only an insufficient focal point displacement.

There has also been an attempt to deform a fitted IOL mechanically by the ciliary muscle, although it has not yet been possible to demonstrate success convincingly.

Another approach attempts to restore the elasticity of the natural eye lens by radial incisions in the crystalline eye lens with a non-invasive FS laser, cf. O. Kermani in "Neues aus Wissenschaft und Forschung", J. Refract Surgery: 2004; 20:651-658. The elasticity is scarcely changed thereby, however, and there is the risk of an induced cataract.

Multifocal IOLs have furthermore been implanted, albeit with the known difficulties, in particular perturbing double images and lack of sharpness since at least two focal lengths with different imaging properties produce simultaneous double images on the retina, cf. "Neue Multifokallinsen, individuelle Lösungen und postoperative Funktionalität", in Der Augenspiegel, September 2004:42-47.

Another attempt to alleviate presbyopia is to produce monovision by refractive laser surgery of the cornea. One eye is in this case corrected to the near point and the other eye is left adjusted to the far point, or corrected so that the latter is then usually the so-called leading eye. Then, however, the two eyes deliver different information which must be processed by the brain and taken in by the patient.

SUMMARY

The present invention adopts another way of restoring the accommodation ability of the human eye.

To this end, the invention provides an intraocular lens whose refractive power can be altered by the application of an electrical voltage. The invention thus relates to an artificial intraocular lens which is suitable for being fitted into the human eye and is configured so that its refractive power can be altered by electrical voltages or fields, so that the accommodation ability of the eye is restored.

In other application fields, so-called liquid lenses have been known for some time. In these, the application of electrical voltages causes a shape change of the liquid lens and therefore a change in its focal length. The underlying physical effect is also referred to as "electro-wetting". The term "liquid lens" in this case also covers other deformable, in particular liquid-like materials. By suitably configured electrodes, selected viscosities and densities of the lens material and by suitable dimensioning of the lens as well as precautions to ensure position stability of the lens, it is possible to achieve a very high dynamic range i.e. a very rapid change of the lens shape; for example, a focal length change frequency in the range of about 2 kHz is already possible at present. Liquid lenses, actuable by electrical voltages, can be produced with diameters in the range of from 3 to 6 mm. Regarding the prior art, reference is made to the following publications in this regard:

Kuiper, S., Hendriks B H W.: Variable-focus Liquid Lens for Miniature Cameras, Appl Phys Lett 2004; 85:1128-1130;

Hecht E., Optics-Second Edition. Addison-Wesley Publishing Company, Chapter 5: Geometrical Optics-Paraxial Theory: p-138;

Krupenkin, T., Yang S., Mach P.: Tunable Liquid Microlens Appl Phys Lett 2003; 82:316-318 and Berge B., Peseux J.: Variable focal lens controlled by an external voltage: An application of electrowetting. Eur Phys J 2000; E3: 159-163.

The intraocular liquid lens according to the invention is dimensioned and configured so that it can be fitted into the capsule of an eye. The intraocular liquid lens may also be dimensioned and configured so that it can be fitted into a sulcus.

The IOL usable in this way furthermore comprises means so that the mechanical surface tension of the lens can be altered by the application of an electrical voltage, in order to change its focal length.

According to a preferred configuration, the lens is dimensioned, and the means for applying an electrical voltage are configured, so that the electrical voltage causes a spherosymmetric deformation of the lens. A radial symmetry is thereby provided in the lens. The lens may also be dimensioned and configured so that the electrical voltages compensate for an astigmatism as well as aberrations, particularly spherical aberrations, i.e. higher-order eye defects.

The so-called "electro-wetting" modifies the surface tension of the liquid or the liquid-like or other suitable material, the lens being configured and/or exposed to external forces so that its shape is changed owing to the modified surface tension, relative to a state without a voltage or with other voltages.

According to particular configurations of the IOL according to the invention, it may be fully or partially covered by a membrane and optionally comprise additional fixing elements, such as the latter is known in conventional intraocular lenses. Fixing elements may be provided on the lens, so that the latter can be positioned in the desired way in the eye.

The shaping of the IOL according to the invention in a capsule in the voltage-free state may be influenced in a desired way by the introduction of supplementary hydrophobic surfaces and a concomitant modification of the surface tension.

According to particular configurations of the invention, the intraocular lens is provided with electrodes for applying the said electrical voltages. The electrodes are in this case at least partially transparent. Also, according to a preferred configuration of the invention, the electrodes are arranged at suitable distances substantially all around the IOL.

The electrical voltages required for controlling the IOLs according to the invention may be obtained and used in various ways. For example, it is possible to use highly miniaturised electronic components. Such components are already implanted nowadays into the human eye, cf. H. G. Sachs and V. P. Gabel in Graefe's Arch. Clin. Exp. Opthalmol. (2004) 242:717-723; article "Die Implantation von Sehprothesen bei progressiven Netzhautdystrophien" by P. Walter, in DER AUGENSPIEGEL, November 2004, p. 32; T. Laube, C. Brockmann, R. Buss, C. Lau, K. Hock, N. Stawski, T. Stieglitz, H. A. Richter and H. Schilling in Graefe's Arch. Clin. Exp. Opthalmol. (2004) 242:661-667; and T. Stieglitz, R. Keller, H. Beutel und J. U. Meyer, "Microsystem Integration Techniques for Intraocular Vision Prostheses Using Flexible Polyimide Foils".

On the other hand, physiological provision of the electrical voltages is also possible: For example, the voltage required for the accommodation may be derived directly from a movement of the eye, in particular by triboelectrical voltage generation i.e. voltage generation by the friction effect. With the aid of an implanted microchip, this voltage may be amplified to the required extent and applied to the suitably configured electrodes of the lens, in order to adjust the surface curvature. For example, the natural accommodation process entails actuation of the ciliary muscle. In the young, fully functional eye, the ciliary muscle causes a deformation of the lens for accommodation. A particular configuration of the present invention provides a means by which an electrical voltage is derived from this action of the ciliary muscle and, if necessary having been amplified sufficiently, is applied to the said electrodes of the lens in order to achieve the desired accommodation as a function of the natural movement of the ciliary muscle.

By a particular arrangement of the invention it is also possible to overcome higher-order imaging defects as well as astigmatic imaging defects, cf. EP 1 091 758 B1 and U.S. Pat. No. 6,369,954 B1.

BRIEF DESCRIPTION OF THE DRAWINGS

Exemplary embodiments of the invention will be described in more detail below with the aid of the drawing, in which.

DETAILED DESCRIPTION

In principle, the change in refractive power or focal length of a lens can be represented by the simple lens equation, the radii of curvature of the lens determining its focal length (cf. for example the textbook by E. Hecht cited above):

$$\frac{1}{f} = (n-1) \cdot \left( \frac{1}{R_1} - \frac{1}{R_2} \right) \quad (1)$$

$R_1$-Radii of curvature of the lens surface $n$-Refractive index

If an intraocular lens (IOL) according to the invention is fitted into the eye's capsule, previously prepared appropriately, then a centred position of the lens in the optical beam path of the eye is essentially obtained. It is also possible to enclose the liquid lens with a suitable membrane and provide it with additional fixing elements, in order to ensure its central position on the optical axis of the eye. This technique is known per se from conventional IOLs.

The change in the refractive power D of a liquid lens can be described by the following equation:

$$D = D_0 + K \frac{U^2}{d} \quad (2)$$

$K$ = Material constant $d$ = Diameter of the lens $U$ = Voltage

The refractive power change of a liquid lens is therefore dependent in principle to the second power on the applied voltage and inversely proportional to the diameter of the lens. For small lens diameters as in this case, and suitable dielectric insulation layers, only relatively small voltages are therefore necessary in order to achieve significant refractive power changes (cf. the article by T. Krupenkin et al. cited above).

In the human eye, the eye lens achieves an accommodation range of from about 10 dpt to about 14 dpt depending on the age.

If currently available electro-optical constants are assumed for the liquid lens material (cf. the above works by S. Kuiper et al., and T. Krupenkin et al.), then such refractive power changes can already be achieved with voltages in the range of U=20-30 V with the materials currently known.

Figure 1:
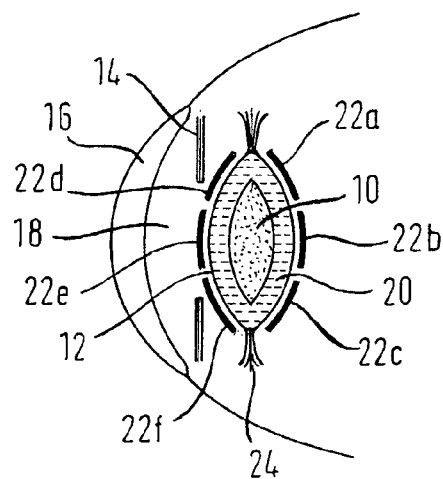
FIG. 1 shows a schematic section through an eye into which an intraocular lens according to the invention is incorporated, the lens not being accommodated.

FIG. 1 shows an intraocular lens 10, which is fitted into a capsule 12 of a human eye. The iris 14, the cornea 16 and the anterior chamber 18 of the eye are furthermore represented.

The intraocular lens 10, made of a liquid material of the type described above, is enclosed by an insulating liquid 20.

Figure 2:
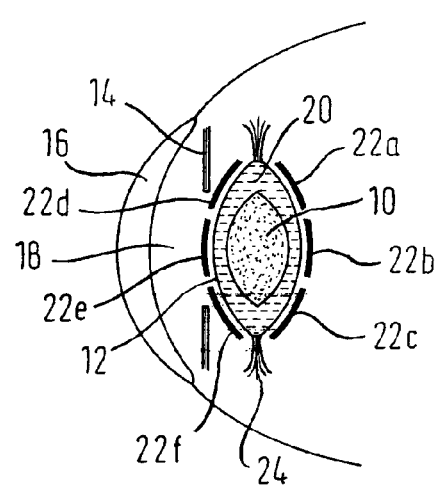
FIG. 2 shows a representation corresponding to FIG. 1, the lens being accommodated.
Figure 3:
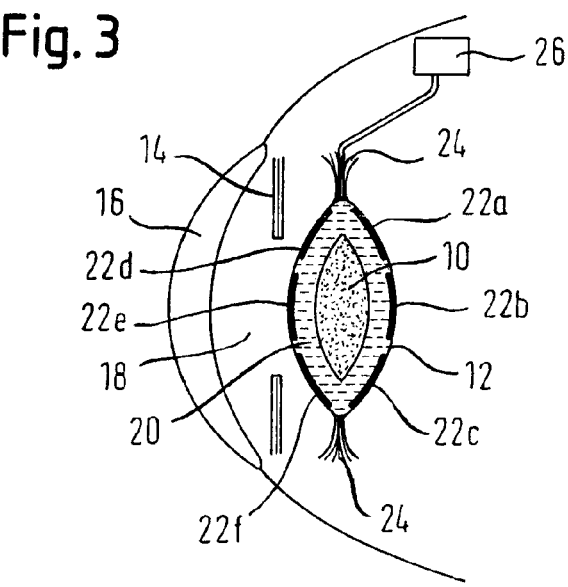
FIG. 3 shows another configuration of an IOL with a microchip for voltage control, again in the incorporated state in the eye, to illustrate the mode of action.

According to the figure, electrodes 22a, 22b, 22c, 22d, 22e, 22f are arranged either around the capsule 12 (FIGS. 1 and 2) or internally on the capsule (FIG. 3). The electrodes may also be arranged in the equatorial plane of the capsule. On the other hand, a completely encapsulated intraocular lens with internally lying electrodes may be used.

The natural ciliary muscle 24 engages on the capsule perpendicularly to the optical axis of the "eye" system.

FIG. 1 schematically shows the unaccommodated state of the intraocular lens 20, i.e. the state in which no voltage is applied to the electrodes and therefore $D=D_0$ applies in Equation (2) above. The stretching force or compressing force F acting perpendicularly to the optical axis is likewise equal to zero F=0.

FIG. 2 shows a state in which a voltage U is applied to the electrodes 22. $D=D_0+KU^2$ applies. The intraocular lens is electrostrictively contracted (accommodated) and a force which is non-zero acts perpendicularly to the optical axis, i.e. it causes the shape change in the desired way so that the radius of curvature of the interface of the lens 10 varies greatly, and the refractive power is therefore increased.

FIG. 3 shows a modified exemplary embodiment in which the system comprises a microchip 26, which is likewise represented in the installed state in FIG. 3. Components which are functionally equivalent or functionally similar to one another are provided with the same references in the figures.

Triboelectrical voltage generation is employed in the exemplary embodiment according to FIG. 3. As described above, a force is associated with the natural accommodation process, for example the force which is exerted by the natural ciliary muscle on the natural eye lens. In the exemplary embodiment according to FIG. 3, a voltage is derived from this force action and is amplified sufficiently, before being applied to the electrodes 22a, ..., 22f so as to cause a corresponding deformation of the interface and therefore accommodation thereof.

The triboelectrical voltage generation may be described in a similar way to the piezoelectric effect, in that case as charge generation by a force and in this case by a movement-initiating force and a charge separation, cf. Benz W., Heinks P., Starke L.: Tabellenbuch Elektronik für Industrie-Elektroniker und Kommunikationselektroniker. Kohl+Noltmeyer Verlag: p. 87. The following applies:

$$\Delta e/e \sim e_{12} \frac{F_{12}}{A} \quad (3)$$

$e_{12}$-Elastic modulus $\Delta e/e$-Relative length change $F_{12}$-Force component $A$-Area $$U = \frac{Q}{C} = \frac{1}{C} S_{12} F_{12} \quad (4)$$

$S_{12}$-Piezoelectric modulus $C$-Capacitance

This triboelectrical voltage generation is amplified via the implanted microchip 26, and this chip is connected via lines (not shown) to the individual electrodes 22a, ..., 22f and controls them so that the desired accommodation is achieved.

What is claimed is:

1. An accommodating intraocular lens assembly with a refractive power that is altered by application of an electrical voltage, the intraocular lens assembly comprising:
    a liquid lens body sized and shaped for implantation within the eye, the liquid lens body having an unaccommodated state in the absence of electrical voltage with a first refractive power, the liquid lens body enclosed by an insulating liquid and configured to be fitted into the capsule of an eye; and
    a plurality of electrodes sized and shaped for implantation within the eye, the plurality of electrodes couplable to said lens body, said electrodes configured to deliver an electrical voltage to said liquid lens body, said liquid lens body having an accommodated state when one or more of said plurality of electrodes is energized with the electrical voltage for changing the surface tension of a liquid or liquid-like material in the liquid lens, said accommodated shape having a second refractive power different from said first refractive power wherein the changed surface tension produces a deformation of the intraocular lens to compensate for an astigmatism or to compensate for higher-order aberrations; and
    a microchip sized and shaped for implantation within the eye, the microchip electrically coupled to said plurality of electrodes, the microchip configured to derive a triboelectrical voltage from a force generated by natural accommodation of the eye, amplify said derived voltage, and apply said amplified voltage to said plurality of electrodes to deform said liquid lens body between said unaccommodated state and said accommodated state such that the intraocular lens assembly provides accommodation as a function of natural movement of a ciliary muscle of the eye associated with the natural accommodation of the eye,
    wherein the surface tension of the liquid or liquid-like material in the liquid lens body is changed by electro-wetting.

2. The intraocular lens assembly of claim 1, further including a means for generating electrical energy.

3. The intraocular lens assembly of claim 1, wherein said plurality of electrodes are arranged in the equatorial plane of the capsule.

4. The intraocular lens assembly of claim 1, wherein said plurality of electrodes are at least partially transparent.

5. The intraocular lens assembly of claim 1, wherein the liquid lens body is covered by a membrane.

6. The intraocular lens assembly of claim 5, wherein the membrane includes a hydrophobic surface.

7. The intraocular lens assembly of claim 1, wherein the plurality of the electrodes are at least partially transparent.

8. The intraocular lens assembly of claim 1, wherein the force from which the voltage is derived is a force exerted on a natural eye lens by the ciliary muscle.

9. A method of implanting an accommodating intraocular lens (IOL) into a human eye, comprising:
    inserting a liquid lens into an optical beam path of the human eye, the liquid lens enclosed by an insulating liquid and configured to be fitted into the capsule of an eye;
    implanting one or more electrodes adjacent to the liquid lens, the one or more electrodes configured to deliver an electrical voltage to the liquid lens;
    implanting a microchip within the eye, the microchip electrically coupled to the one or more electrodes; and
    applying a voltage to the one or more electrodes for changing the surface tension of a liquid or liquid-like material in the lens in order to adjust the curvature of the liquid lens to produce a deformation of the intraocular lens that compensates for an astigmatism or compensates for higher-order aberrations, wherein the applied voltage is triboelectrical voltage generated from a force generated by natural accommodation of the eye such that the adjustable intraocular lens provides accommodation as a function of natural movement of a ciliary muscle of the eye associated with the natural accommodation of the eye, wherein the microchip amplifies the triboelectrical voltage and applies the amplified triboelectrical voltage to the one or more electrodes to adjust the curvature of the liquid lens, and wherein the surface tension of the liquid or liquid-like material in the liquid lens is changed by electro-wetting.

10. The method of claim 9, further including arranging the one or more electrodes in the equatorial plane of a capsule of the human eye.

11. The method of claim 9, wherein said implanting includes positioning at least one electrode on the exterior of a capsule of the human eye.

12. The method of claim 9, wherein said implanting includes positioning at least one electrode on the interior of a capsule of the human eye.

13. The method of claim 9, further including implanting said insulating liquid between the liquid lens and the electrodes.

* * * * *